(12) United States Patent
Haga et al.

(10) Patent No.: US 6,300,323 B1
(45) Date of Patent: Oct. 9, 2001

(54) (POLY)ETHEREAL AMMONIUM SALTS OF HERBICIDES BEARING ACIDIC MOIETIES AND THEIR USE AS HERBICIDES

(75) Inventors: Takahiro Haga; Kevin E. Crosby, both of Concord; Jeffrey R. Schussler, Chardon, all of OH (US)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 09/634,630

(22) Filed: Aug. 8, 2000

(51) Int. Cl.$^7$ ............................ A01N 57/12; C07C 229/06

(52) U.S. Cl. ............................. 514/76; 514/114; 562/553

(58) Field of Search ............................... 562/553; 514/76, 514/114

(56) References Cited

U.S. PATENT DOCUMENTS

| | | |
|---|---|---|
| 3,799,758 | 3/1974 | Franz . |
| 3,853,530 | 12/1974 | Franz . |
| 4,140,513 | 2/1979 | Prill . |
| 4,315,765 | 2/1982 | Large . |
| 4,405,531 | 9/1983 | Franz . |
| 4,481,026 | 11/1984 | Prisbylla . |
| 4,507,250 | 3/1985 | Bakel . |
| 5,750,468 * | 5/1998 | Wright et al. ............... 504/206 |

FOREIGN PATENT DOCUMENTS

WO 99/05914    2/1999    (WO) .

* cited by examiner

*Primary Examiner*—Johann Richter
*Assistant Examiner*—Brian J. Davis
(74) *Attorney, Agent, or Firm*—Sughrue, Mion, Zinn, Macpeak & Seas, PLLC

(57) ABSTRACT

A compound

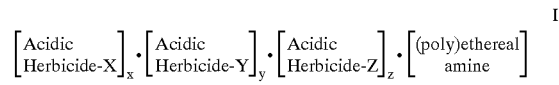

Wherein x, y, and z are integers from 0 to 3; and
the (poly)ethereal amine is at least one selected from compounds of formula $II^1$ through $II^5$:

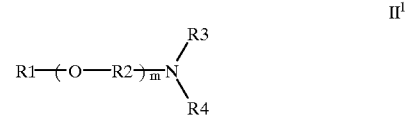

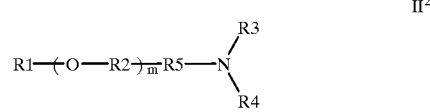

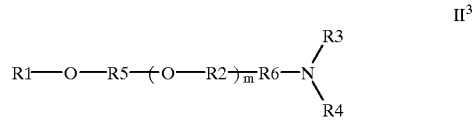

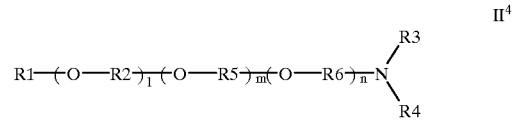

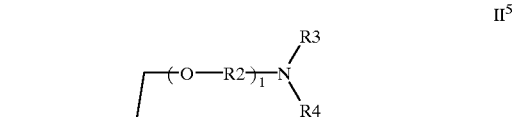

6 Claims, No Drawings

(POLY)ETHEREAL AMMONIUM SALTS OF HERBICIDES BEARING ACIDIC MOIETIES AND THEIR USE AS HERBICIDES

BACKGROUND OF THE INVENTION

Some herbicides bearing acidic moieties are known to be highly effective and commercially important herbicides useful for combating the presence of a wide variety of unwanted vegetation, including agricultural weeds.

Since usually, such acidic herbicides have low solubility in water, they are applied as their derivatives such as metal salts or ammonium salts to enhance the solubility, or esters or amides to enhance movement into plant. For example, N-phosphonomethyl-glycine is formulated in commercial compositions in the form of a water-soluble salt. Herbicidal amine salts of N-phosphonomethylglycine are disclosed, for example, in U.S. Pat. Nos. 3,799,758, 3,853,530, 4,140,513, 4,315,765, 4,405,531, 4,481,026, and 4,507,250. These salts are claimed to have uses as plant regulators, herbicides and defoliants. Many of these salts have the counter-cation to N-phosphonomethylglycine anion bearing relatively low molecular weight. Typical of such salts are alkali metal, for example sodium and potassium salts; ammonium salt; and numerous salts having an ammonium, sulfonium or sulfoxonium cation with 1–3 organic groups containing in total 1–6 carbon atoms, for example 2-propylammonium (isopropylammonium), ethanolammonium, ethylenediammonium, trimethylsulfonium or trimethylsulfoxonium.

Recent Patent WO 99/05914 reveals the herbicidal compositions promoting herbicidal effectiveness of exogeneous chemical substances. The compositions are the amphiphilic salts having anions of the parent exogeneous chemical substances and cations derived by protonation of one or more polyamine(s) or polyamine derivative(s) each having (a) at least two nitrogen-containing groups, of which a number n not less than 1 are amino groups that can be protonated to form cationic primary, secondary, or tertiary ammonium groups, and (b) at least one hydrocarbyl or acyl group having about 6 to 30 carbon atoms.

BRIEF DESCRIPTION OF THE INVENTION

A preferred group of the acidic herbicide consists of those that are normally applied post-emergence to foliage of plants. An especially preferred group of foliar-applied herbicide consists of those that are systemic in plants, that is, translocated to some extent from their point of entry in the foliage to other parts of the plant where they can usefully exert their herbicidal effect.

This invention relates to the enhancement of the activity of acidic herbicides by the formation of salts using (poly)ethereal amine compounds and also to a method of controlling undesirable vegetation by applying a herbicidally effective amount of the (poly)ethereal amine salts to such vegetation when the latter is in a post-emergent state. These (poly)ethereal ammonium salts are thought to aid the penetration and transport of acidic herbicides into and throughout the plant. These salts contain anions derived from parent herbicides and amphiphilic (poly)ethereal ammonium cation(s). These features are proved to enhance the activity of acidic herbicides.

The term "herbicidally effective amount" designates any amount of the compounds disclosed herein, which will kill a plant or any portion thereof. By "plants" is meant germinating seeds, emerging seedlings, and established vegetation, including roots and above ground-portions.

By the term "post-emergent" as used herein, is meant the application of the herbicide compound to weed pests, after these pests have emerged from the ground.

The present invention provides a (poly)ethereal ammonium salt of acidic herbicides of the following formula I:

Wherein x, y, and z are integers from 0 to 3 with the proviso that $0 < x+y+z \leq 3$.

Acidic Herbicide-X, Acidic Herbicide-Y, and Acidic Herbicide-Z, same or different that can be used in compositions of the present invention and possess the dissociable proton(s) in their structures include, but are not limited to, the following herbicides.

acifluorfen, asulam, benazolin, bentazon, bilanafos, bromacil, bromoxynil, chloramben, clopyralid, cyhalofop, 2,4-D, 2,4-DB, dalapon, dicamba, dichlorprop, diclofop, DNOC, endothall, fenac, fenoxaprop, flamprop, fluazifop, flumiclorac, fluoroglycofen, fomesafen, fosamine, glufosinate, glyphosate, haloxyfop, imazameth, imazamethabenz, imazamox, imazapic, imazapyr, imazaquin, imazethapyr, ioxynil, MCPA, MCPB, MCPP, mecoprop, methylarsonic acid, naptalam, nonanoic acid, picloram, quinclorac, quizalofop, sulfamic acid, 2,3,6-TBA, TCA, and triclopyr.

The (poly)ethereal amine(s) II or derivative(s) thereof are preferably selected from compounds of formula $II^1$ through $II^5$:

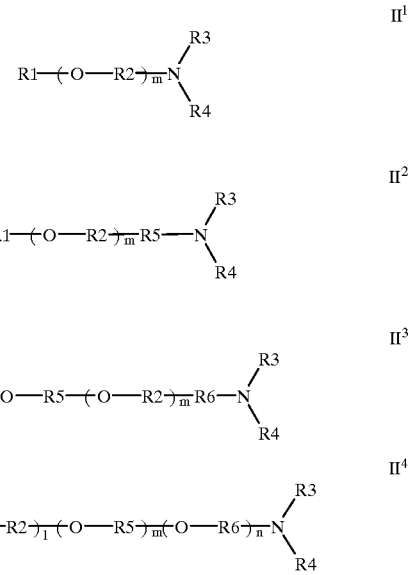

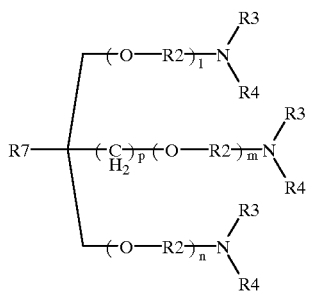

wherein $R_1$ is a hydrogen, a $C_{1-26}$ alkyl, a $C_{2-6}$ alkenyl, a $C_{2-6}$ alkynyl branched-chain or straight-chain which may or may not be substituted with one or more halogen, hydroxy, $C_{1-6}$ alkoxy, ($C_{1-6}$ alkyl-)$_q$-amino ($q$ is an integer of 0, 1, or 2), morpholino, or $C_{1-6}$ alkoxycarbonyl group, an aryl, or a heteroaryl which may or may not be substituted with $C_{1-6}$ alkyl, $C_{1-6}$ haloalkyl, halogen, $C_{1-6}$ alkoxy, ($C_{1-6}$ alkyl-)$_q$-amino ($q$ is an integer of 0, 1, or 2), nitro, or $C_{1-6}$ alkoxycarbonyl group;

$R_2$, $R_5$, and $R_6$ are independently $C_{1-8}$ alkylene branched-chain or straight-chain, which may contain imine or ether linkage therein and may be substituted by a $C_{1-6}$ alkyl group.

$R_3$ and $R_4$ are a hydrogen atom or a $C_{1-6}$ alkyl group, which may be branched or straight and may or may not be substituted with one or more $C_{1-6}$ alkoxy, or a group Of $R_1$—(—O—$R_2$—)$_{m'}$—O—.

$R_7$ is a hydrogen or a $C_{1-6}$ alkyl group.

l, m and n is a number from 1 to about 500.

m' is a number from 0 to about 35.

p is an integer of 0 or 1.

When m is 1, none of $R_1$, $R_3$, and $R_4$ is H and furter $R_2$ is not ethylene.

Many of these (poly)ethereal amine exist as steric or enantiomeric isomers and this invention covers all forms and mixtures of the aforementioned compounds. Most of the (poly)ethereal amines and their derivatives are commercially available. New (poly)ethereal amines II$^6$ bearing (hetero)aryl moiety were synthesized by the following reaction between (hetero)aryl halide and hydroxyl-amine.

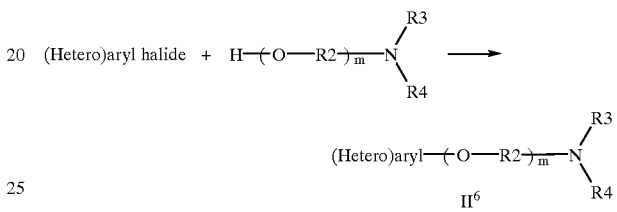

The examples of the (poly)ethereal amines II include, but are not limited to, the following (poly)ethereal amines in Tables-1 through -5.

TABLE 1

(poly)ethereal amines II$^1$ $$R_1\!-\!(\!-\!O\!-\!R_2\!-\!)_m\!-\!N\!\!\begin{array}{c}R_3\\R_4\end{array}$$

| No. | $R_1$ | $R_2$ | m | $R_3$ | $R_4$ |
|---|---|---|---|---|---|
| 1-1 | H | —CH$_2$CH$_2$CH$_2$— | 1 | —CH$_2$CH$_3$ | —CH$_2$CH$_3$ |
| 1-2 | H | —CH$_2$CH$_2$CH$_2$— | 2 | H | H |
| 1-3 | H | —CH$_2$CH$_2$CH$_2$NHCH$_2$CH$_2$CH$_2$— | 1 | H | H |
| 1-4 | H | —CH(CH$_3$)CH$_2$CH$_2$CH$_2$CH$_2$— | 1 | —CH$_2$CH$_3$ | —CH$_2$CH$_3$ |
| 1-5 | H | —C(CH$_3$)$_2$CH$_2$CH$_2$CH$_2$CH(CH$_3$)— | 1 | H | H |
| 1-6 | H | —CH$_2$CH$_2$CH$_2$— | 10 | H | H |

TABLE 1-continued
(poly)ethereal amines II[1]
$$R_1\!-\!(\!O\!-\!R_2\!)_m\!-\!N\!\begin{array}{c}R_3\\R_4\end{array}$$
| No. | R₁ | R₂ | m | R₃ | R₄ |
|---|---|---|---|---|---|
| 1-7 | H₃C— | 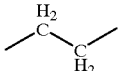 | 16.34 | H | H |
| 1-8 | H₃C— | 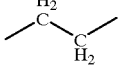 | 44.75 | H | H |
| 1-9 | 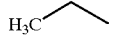 | 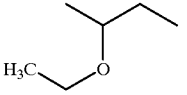 | 1 | H | H |
| 1-10 | 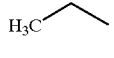 | 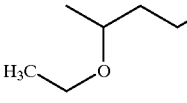 | 1 | H | 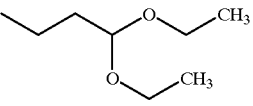 |
| 1-11 | 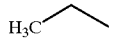 | 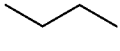 | 3 | H | 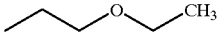 |
| 1-12 | 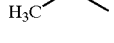 | 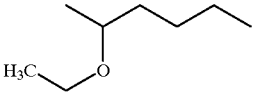 | 1 | H | H |
| 1-13 | 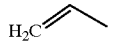 | 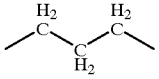 | 1 | H | H |
| 1-14 | 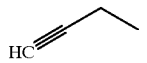 | 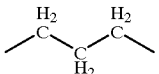 | 5 | H | H |
| 1-15 | 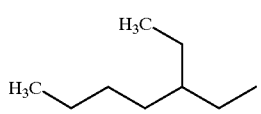 | 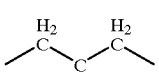 | 1 | H | H |
| 1-16 | (n)-C₁₂H₂₅— | 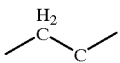 | 2 | H | H |
| 1-17 | (n)-C₁₂H₂₅— | 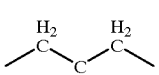 | 1 | H | H |
| 1-18 | (n)-C₁₂H₂₅— | 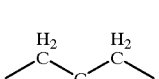 | 35 | H | H |

TABLE 1-continued (poly)ethereal amines II[1]

$$R1\text{-}(\text{O}\text{-}R2)_m\text{-}N\begin{smallmatrix}R3\\R4\end{smallmatrix}$$

| No. | R₁ | R₂ | m | R₃ | R₄ |
|---|---|---|---|---|---|
| 1-19 | F₃C–CH₂–CH₂– | CH₃–CH(OCH₂CH₃)–CH₂–CH₂–CH₂– (sec-hexyl with ethoxy) | 15 | —CH₃ | —CH₃ |
| 1-20 | H₂N–CH₂–CH₂– | –CH₂–CH(CH₃)–CH₂– | 2 | H | H |
| 1-21 | H₂N–CH₂–CH₂–CH₂– | –CH₂–CH₂–CH₂– | 1 | H | H |
| 1-22 | (H₃C–CH₂)₂N–CH₂–CH₂–CH₂– | –CH₂–CH₂–CH₂– | 26 | H | H |
| 1-23 | H₂N–CH(CH₃)–CH₂– | 3-(CF₃)-1-methyl-pyrazol-5-yl– | 33.1 | H | H |
| 1-24 | H₂N–CH(CH₃)–CH₂– | –CH₂–CH(CH₃)–CH₂– | 2.6 | H | H |
| 1-25 | H₂N–CH(CH₃)–CH₂– | –CH₂–CH(CH₃)–CH₂– | 5.6 | H | H |
| 1-26 | morpholino–CH₂–CH₂–CH₂– | –CH₂–CH(CH₃)–CH₂– | 1 | H | H |
| 1-27 | HO–(CH₂)₁₂– | –CH₂–CH₂–CH₂– | 2 | –CH₂CH₃ | –CH₂CH₃ |
| 1-28 | CH₃–(CH₂)₁₁–O–CH₂–CH₂–CH₂–NH–CH₂–CH₂– | –CH₂–CH₂–CH₂– | 1 | H | H |
| 1-29 | CH₂=C(CH₃)–C(=O)– | –CH₂–CH₂–CH₂– | 1 | –CH₂CH₃ | –CH₂CH₃ |

TABLE 1-continued
(poly)ethereal amines II[1]
| No. | R₁ | R₂ | m | R₃ | R₄ |
|---|---|---|---|---|---|
| 1-30 | 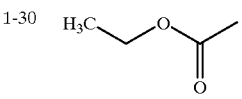 | 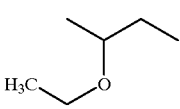 | 1 | H | H |
| 1-31 | 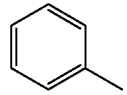 | 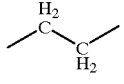 | 1 | H | H |
| 1-32 | 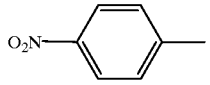 | 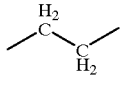 | 6 | H | H |
| 1-33 | 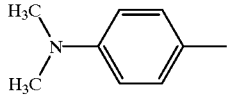 | 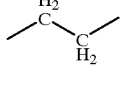 | 10 | H | H |
| 1-34 | 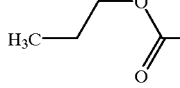 | 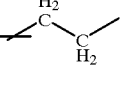 | 6 | H | H |
| 1-35 | 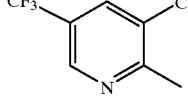 | 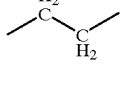 | 2 | H | H |
| 1-36 | 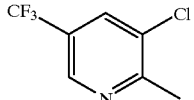 | 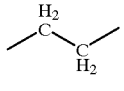 | 1 |  |  |
| 1-37 | 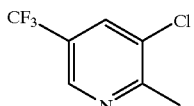 | 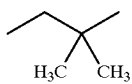 | 1 | H | H |
| 1-38 | 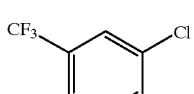 | 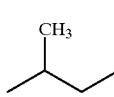 | 1 |  |  |
| 1-39 | 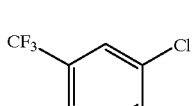 | 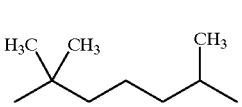 | 1 | H | H |
| 1-40 | 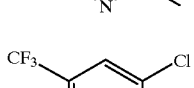 | 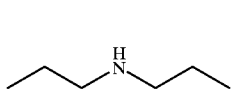 | 1 | H | H |

TABLE 1-continued
(poly)ethereal amines II[1]
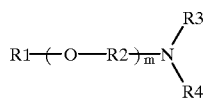
| No. | R₁ | R₂ | m | R₃ | R₄ |
|---|---|---|---|---|---|
| 1-41 | ![pyrimidin-2-yl] | -CH₂-CH₂- | 1 | -CH₂CH₂CH₃ | -CH₂CH₂CH₃ |
| 1-42 | 5-CF₃-pyrimidin-2-yl | -CH₂-CH₂- | 2 | -CH₂CH₂CH₃ | -CH₂CH₂CH₃ |
| 1-43 | 3-CF₃-1-methyl-5-pyrazolyl | -CH₂-CH₂- | 3 | -CH₂CH₂CH₃ | -CH₂CH₂CH₃ |
| 1-44 | 2,6-dimethylpyridin-3-yl | -CH₂-CH₂- |  | -(n)-C₆H₁₃ | -(n)-C₆H₁₃ |
| 1-45 | methyl 2-methylnicotinate-yl | -CH₂-CH₂- |  | -(n)-C₆H₁₃ | -(n)-C₆H₁₃ |
| 1-46 | H₃C— | -CH₂-CH₂- | 112.93 | H | H |
| 1-47 | H₃C— | -CH₂-CH₂- | 226.56 | H | H |
| 1-48 | H₃C— | -CH₂-CH₂- | 453.84 | H | H |

TABLE 2

(poly)ethereal amines II[2]

$$R_1-(O)_m-R_2-R_5-N(R_3)(R_4)$$

| No. | R₁ | R₂ | R₃ | R₄ | R₅ | m |
|---|---|---|---|---|---|---|
| 2-1 | H₃C— | —CH(R)—CH₂— (R, H/CH₃ = 1/9) | H | H | —CH₂—CH(CH₃)—O— | 9 |
| 2-2 | H₃C— | —CH(R)—CH₂— (R, H/CH₃ = 19/3) | H | H | —CH₂—CH(CH₃)—O— | 19.85 |
| 2-3 | H₃C—(O—)₆ | —CH(R)—CH₂— (R, H/CH₃ = 7/3) | H | H | —CH₂—CH(CH₃)—O— | 34.17 |
| 2-4 | H₃C— | —CH₂CH₂CH₂— | H | H | —CH₂—CH(CH₃)—O— | 5 |
| 2-5 | H₃C— | —CH(CH₃)—CH₂— | —CH₂CH₃ | —CH₂CH₃ | —CH₂—CH(CH₃)—O— | 25 |
| 2-6 | H₃C— | —CH(CH₃)—CH₂— | H | H | —CH₂—CH(CH₃)—O— | 45 |
| 2-7 | H₃C—(O—)₆ | —CH₂CH₂CH₂— | H | H | —CH₂—CH(CH₃)—O— | 15 |
| 2-8 | H₃C—(O—)₆ | —CH(CH₃)—CH₂— | —CH₂CH₃ | —CH₂CH₃ | —CH₂—CH(CH₃)—O— | 35 |
| 2-9 | H₃C—(O—)₆ | —CH(CH₃)—CH₂— | H | H | —CH₂—CH(CH₃)—O— | 55 |
| 2-10 | H₃C— | —CH(R)—CH₂— (R, H/CH₃ = 19/3) | H | H | —CH₂—CH(CH₃)—O— | 63.3 |
| 2-11 | (n)-C₁₂H₂₅— | —CH(CH₃)—CH₂— | —CH₂CH₃ | —CH₂CH₃ | —CH₂—CH₂—O— | 35 |

TABLE 2-continued
(poly)ethereal amines II²
$$R1-(O)_m-R2-R5-N\begin{matrix}R3\\R4\end{matrix}$$
| No. | R₁ | R₂ | R₃ | R₄ | R₅ | m |
|---|---|---|---|---|---|---|
| 2-12 | 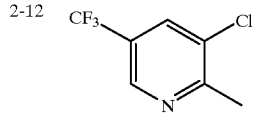 | 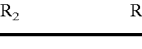 | —CH₃ | —CH₃ |  | 5 |
TABLE 3
(poly)ethereal amines II³
$$R1-O-R5-(O-R2)_m-R6-N\begin{matrix}R3\\R4\end{matrix}$$
| No. | R₁ | R₂ | R₃ | R₄ | R₅ | R₆ | m |
|---|---|---|---|---|---|---|---|
| 3-1 |  | 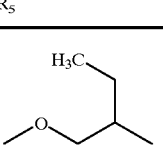 | H | H | 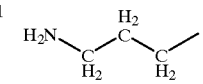 | 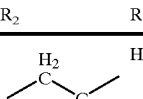 | 1 |
| 3-2 | H₃C— |  | H | H |  | 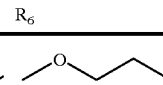 | 8 |
| 3-3 | H₃C— |  | H | H |  |  | 8 |
| 3-4 | H₃C— |  | H | H |  | 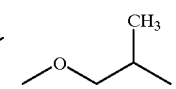 | 15 |
| 3-5 | H₃C— |  | H | H |  |  | 35 |
| 3-6 | H₃C— |  | —CH₃ | —CH₃ |  | 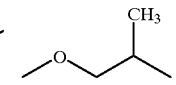 | 55 |
| 3-7 |  |  | H | H |  |  | 20 |
| 3-8 |  | 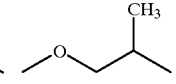 | —CH₃ | —CH₃ |  |  | 15 |

TABLE 4

(poly)ethereal amines II[4]

$$R1{-}(O{-}R2)_l{-}(O{-}R5)_m{-}(O{-}R6)_n{-}N(R3)(R4)$$

| No. | R$_1$ | R$_2$ | R$_3$ | R$_4$ | R$_5$ | R$_6$ | l | n | m |
|---|---|---|---|---|---|---|---|---|---|
| 4-1 | CH$_3$CH(NH$_2$)CH$_3$ | isobutyl (CH$_3$CH(CH$_3$)CH$_2$–) | H | H | n-butyl | isobutyl (–CH$_2$CH(CH$_3$)–) | l + n = 3.6 | | 9 |
| 4-2 | CH$_3$CH(NH$_2$)CH$_3$ | isopropyl (CH$_3$CH(CH$_3$)–) | –CH$_3$ | –CH$_3$ | n-butyl | sec-butyl (–CH(CH$_3$)CH$_2$CH$_3$) | 5 | 5 | 5 |
| 4-3 | CH$_3$OCH(CH$_3$)CH$_2$– | isobutyl | H | H | isobutyl | n-butyl | 2 | 4 | 6 |
| 4-4 | CH$_3$OCH(CH$_3$)CH$_2$– | n-pentyl | –CH$_2$CH$_3$ | –CH$_2$CH$_3$ | isobutyl | sec-butyl | 3 | 5 | 7 |

TABLE 5

(poly)ethereal amines II[5]

$$R7{-}\Big[{-}(O)_l{-}R2{-}N(R3)(R4)\Big]$$
$$\phantom{R7}{-}(CH_2)_p{-}O{-}(R2)_m{-}N(R3)(R4)$$
$$\phantom{R7}{-}(O{-}R2)_n{-}N(R3)(R4)$$

| No. | R$_2$ | R$_3$ | R$_4$ | R$_7$ | l | m | n | p |
|---|---|---|---|---|---|---|---|---|
| 5-1 | isobutyl | H | H | C$_2$H$_5$– | l + m + n = 5.2 | | | 1 |
| 5-2 | isobutyl | H | H | H | l + m + n = 50 | | | 0 |
| 5-3 | n-butyl | –CH$_3$ | –CH$_3$ | (n)-C$_6$H$_{13}$– | l + m + n = 10 | | | 1 |
| 5-4 | n-butyl | –CH$_2$CH$_3$ | –CH$_2$CH$_3$ | H$_3$C– | l + m + n = 80 | | | 0 |

These (poly)ethereal amines will react with one or more molar equivalent of acidic herbicide(s). The generated (poly)ethereal ammonium salts may be isomeric or complex mixtures and all forms of these salts are claimed.

These salts will have the formula I:

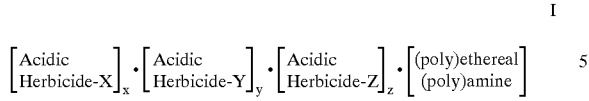

Wherein x, y, and z are integers from 0 to 3 with the proviso that $1 \leq x+y+z \leq 3$.

Acidic Herbicide-X, Acidic Herbicide-Y, and Acidic Herbicide-Z, same or different that can be used in compositions of the present invention and possess the dissociable proton(s) in their structures include, but are not limited to, the following herbicides.

acifluorfen, asulam, benazolin, bentazon, bilanafos, bromacil, bromoxynil, chloramben, clopyralid, cyhalofop, 2,4-D, 2,4-DB, dalapon, dicamba, dichlorprop, diclofop, DNOC, endothall, fenac, fenoxaprop, flamprop, fluazifop, flumiclorac, fluoroglycofen, fomesafen, fosamine, glufosinate, glyphosate, haloxyfop, imazameth, imazamethabenz, imazamox, imazapic, imazapyr, imazaquin, imazethapyr, ioxynil, MCPA, MCPB, MCPP, mecoprop, methylarsonic acid, naptalam, nonanoic acid, picloram, quinclorac, quizalofop, sulfamic acid, 2,3,6-TBA, TCA, and triclopyr.

The (poly)ethereal amine(s) II or derivative(s) thereof are preferably selected from compounds of formula II$^1$ through II$^5$:

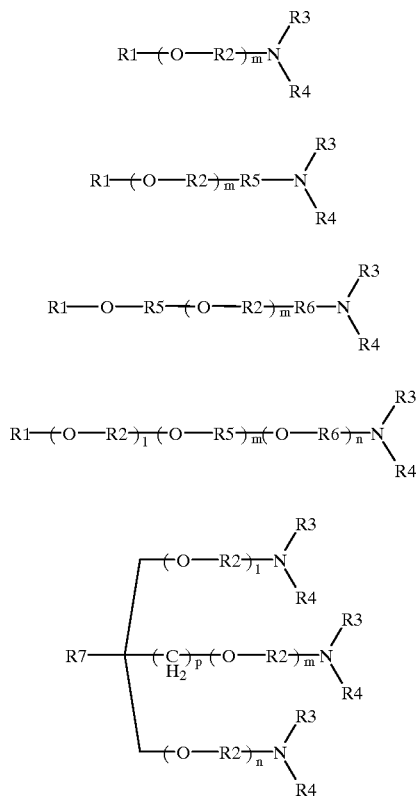

wherein $R_1$ is a hydrogen, a $C_{1-26}$ alkyl, a $C_{2-6}$ alkenyl, a $C_{2-6}$ alkynyl branched-chain or straight-chain which may or may not be substituted with one or more halogen, hydroxy, $C_{1-6}$ alkoxy, ($C_{1-6}$ alkyl-)$_q$-amino ($q$ is an integer of 0, 1, or 2), morpholino, or $C_{1-6}$ alkoxycarbonyl group, an aryl, or a heteroaryl which may or may not be substituted with $C_{1-6}$ alkyl, $C_{1-6}$ haloalkyl, halogen, $C_{1-6}$ alkoxy, ($C_{1-6}$ alkyl-)$_q$-amino ($q$ is an integer of 0, 1, or 2), nitro, or $C_{1-6}$ alkoxycarbonyl group;

$R_2$, $R_5$, and $R_6$ are independently $C_{1-8}$ alkylene branched-chain or straight-chain, which may contain imine or ether linkage therein and may be substituted by a $C_{1-6}$ alkyl group.

$R_3$ and $R_4$ are a hydrogen atom or a $C_{1-6}$ alkyl group, which may be branched or straight and may or may not be substituted with one or more $C_{1-6}$ alkoxy, or a group of $R_1$—(—O—$R_2$—)$_{m'}$—O—.

$R_7$ is a hydrogen or a $C_{1-6}$ alkyl group.

l, m and n is a number from 1 to about 500.

m' is a number from 0 to about 35.

p is an integer of 0 or 1.

When m is 1, none of $R_1$, $R_3$, and $R_4$ is H and further $R_2$ is not ethylene.

The examples of the (poly)ethereal ammonium salts I of this invention include, but are not limited to, the following (poly)ethereal ammonium salts in Table-6.

TABLE 6

(poly)ethereal ammonium salts I

| No. | (poly) ethereal amine used | Acidic Herbicide-X | Acidic Herbicide-Y | Acidic Herbicide-Z | Molar Ratio of Amine/ Herbicide-X/ Herbicide-Y/ Herbicide-Z |
|---|---|---|---|---|---|
| 6-1 | 1-1 | glyphosate | — | — | 1/1/0/0 |
| 6-2 | 1-2 | glyphosate | — | — | 1/1/0/0 |
| 6-3 | 1-3 | glyphosate | — | — | 1/1/0/0 |
| 6-4 | 1-4 | glyphosate | — | — | 1/1/0/0 |
| 6-5 | 1-5 | glyphosate | — | — | 1/1/0/0 |
| 6-6 | 1-7 | glyphosate | — | — | 1/1/0/0 |
| 6-7 | 1-8 | glyphosate | — | — | 1/1/0/0 |
| 6-8 | 1-9 | glyphosate | — | — | 1/1/0/0 |
| 6-9 | 1-10 | glyphosate | — | — | 1/1/0/0 |
| 6-10 | 1-12 | glyphosate | — | — | 1/1/0/0 |
| 6-11 | 1-13 | glyphosate | — | — | 1/1/0/0 |
| 6-12 | 1-15 | glyphosate | — | — | 1/1/0/0 |
| 6-13 | 1-16 | glyphosate | — | — | 1/1/0/0 |
| 6-14 | 1-17 | glyphosate | — | — | 1/1/0/0 |
| 6-15 | 1-20 | glyphosate | — | — | 1/1/0/0 |
| 6-16 | 1-21 | glyphosate | — | — | 1/1/0/0 |
| 6-17 | 1-23 | glyphosate | — | — | 1/1/0/0 |
| 6-18 | 1-24 | glyphosate | — | — | 1/1/0/0 |
| 6-19 | 1-25 | glyphosate | — | — | 1/1/0/0 |
| 6-20 | 1-28 | glyphosate | — | — | 1/1/0/0 |
| 6-21 | 1-29 | glyphosate | — | — | 1/1/0/0 |
| 6-22 | 1-31 | glyphosate | — | — | 1/1/0/0 |
| 6-23 | 1-35 | glyphosate | — | — | 1/1/0/0 |
| 6-24 | 1-36 | glyphosate | — | — | 1/1/0/0 |
| 6-25 | 1-37 | glyphosate | — | — | 1/1/0/0 |
| 6-26 | 1-38 | glyphosate | — | — | 1/1/0/0 |
| 6-27 | 1-39 | glyphosate | — | — | 1/1/0/0 |
| 6-28 | 1-40 | glyphosate | — | — | 1/1/0/0 |
| 6-29 | 1-41 | glyphosate | — | — | 1/1/0/0 |
| 6-30 | 2-1 | glyphosate | — | — | 1/1/0/0 |
| 6-31 | 2-2 | glyphosate | — | — | 1/1/0/0 |
| 6-32 | 3-1 | glyphosate | — | — | 1/1/0/0 |
| 6-33 | 3-2 | glyphosate | — | — | 1/1/0/0 |
| 6-34 | 2-3 | glyphosate | — | — | 1/1/0/0 |
| 6-35 | 4-1 | glyphosate | — | — | 1/1/0/0 |
| 6-36 | 5-1 | glyphosate | — | — | 1/1/0/0 |
| 6-37 | 5-2 | glyphosate | — | — | 1/1/0/0 |
| 6-38 | 3-1 | glyphosate | — | — | 1/2/0/0 |
| 6-39 | 1-24 | glyphosate | — | — | 1/2/0/0 |
| 6-40 | 1-25 | glyphosate | — | — | 1/2/0/0 |

TABLE 6-continued (poly)ethereal ammonium salts I

| No. | (poly) ethereal amine used | Acidic Herbicide-X | Acidic Herbicide-Y | Acidic Herbicide-Z | Molar Ratio of Amine/ Herbicide-X/ Herbicide-Y/ Herbicide-Z |
|---|---|---|---|---|---|
| 6-41 | 1-20 | glyphosate | — | — | 1/2/0/0 |
| 6-42 | 1-23 | glyphosate | — | — | 1/2/0/0 |
| 6-43 | 5-1 | glyphosate | — | — | 1/2/0/0 |
| 6-44 | 5-1 | glyphosate | — | — | 1/3/0/0 |
| 6-45 | 5-2 | glyphosate | — | — | 1/2/0/0 |
| 6-46 | 5-2 | glyphosate | — | — | 1/3/0/0 |
| 6-47 | 1-23 | glyphosate | 2,4-D | — | 1/1/1/0 |
| 6-48 | 5-2 | glyphosate | 2,4-D | — | 1/1/1/0 |
| 6-49 | 5-1 | glyphosate | 2,4-D | — | 1/1/1/0 |
| 6-50 | 5-1 | glyphosate | 2,4-D | — | 1/1.5/1.5/0 |
| 6-51 | 1-23 | glyphosate | Phenyl acetic acid | — | 1/1/1/0 |
| 6-52 | 1-23 | glyphosate | 2,4-D | — | 3.5/2.5/1/0 |
| 6-53 | 1-23 | glyphosate | 2,4-D | — | 2.5/2.5/1/0 |
| 6-54 | 1-23 | glyphosate | dicamba | — | 2.5/2.5/0.55/0 |
| 6-55 | 1-23 | glyphosate | acifluorfen | — | 2.5/2.5/0.4/0 |
| 6-56 | 1-23 | glyphosate | quinclorac | — | 2.5/2.5/2/0 |
| 6-57 | 3-1 | glyphosate | MCPB | — | 1/1/1/0 |
| 6-58 | 5-1 | 2,4-D | MCPB | dicamba | 2/2/1/1 |
| 6-59 | 5-1 | glyphosate | 2,4-D | picloram | 1/1/1/1 |
| 6-60 | 5-2 | glyphosate | MCP | tribac | 1/1/1/1 |
| 6-61 | 5-1 | glyphosate | 2,4-D | picloram | 2.5/2.5/1/0.25 |
| 6-62 | 2-2 | glyphosate | 2,4-DB | picloram | 311/1/1 |
| 6-63 | 2-3 | glyphosate | MCPA | picloram | 3/1/1/1 |
| 6-64 | 2-2 | glyphosate | 2,4-D | picloram | 3.75/2.5/1/0.25 |
| 6-65 | 2-2 | glyphosate | MCPA | Dicamba | 3.80/2.5/0.75/0.5 |
| 6-66 | 2-2 | glyphosate | 2,4-DB | glufosinate | 3.9/2.5/0.5/0.9 |
| 6-67 | 2-2 | glyphosate | MCPB | picloram | 3.3/2.5/0.55/0.25 |
| 6-68 | 3-2 | glyphosate | MCPP | picloram | 3/1/1/1 |
| 6-69 | 2-2 | glufosinate | — | — | 1/1/0/0 |
| 6-70 | 3-1 | glufosinate | — | — | 1/0.9/0/0 |
| 6-71 | 3-2 | glufosinate | — | — | 1/1/0/0 |
| 6-72 | 2-3 | glufosinate | — | — | 1/0.9/0/0 |
| 6-73 | 2-2 | bilanafos | — | — | 1/1/0/0 |
| 6-74 | 3-1 | bilanafos | — | — | 1/1.5/0/0 |
| 6-75 | 3-2 | bilanafos | — | — | 1/1/0/0 |
| 6-76 | 2-3 | bilanafos | — | — | 1/1.5/0/0 |

SYNTHESIS

Typically these salts are normally formed by spontaneous exothermic salt formation by dissolving or suspending the acids in water at between room temperature −100° C. with or without a water miscible co-solvent such as acetone, dioxane, dimethyl-sulfoxide, tetrahydrofuran, N,N-dimethylformamide, ethylene glycol, an alcohol such as methanol, ethanol or 2-propanol when a quantity of the (poly)ethereal amine is introduced with or without a small amount of the water miscible solvent. After, if necessary, heating for between 0.5 and 2 hours the solution is cooled. Either thus obtained aqueous solution itself or solid salt obtained after evaporation of water to dryness in the presence of an anti foaming agent can be used for the activity tests.

Preparation Examples for the compounds of the present invention will be described. All temperatures are measured in ° C.

SYNTHESIS EXAMPLE
Example 1

Synthesis of N-(Phosphonomethyl)glycine. 2-(3-chloro-5-trifluoromethyl-2-pyridyloxy)-ethyl diethyl amine salt: Compound 6-24

Step-1. Synthesis of the intermediate, 2-(3-chloro-5-trifluoromethyl-2-pyridyloxy)-ethyl diethyl amine: Compound 1-36

To the mixture of sodium hydride(528 mg, 22 mmol) in 25 ml of anhydrous tetrahydrofuran was added N,N-diethyl-ethanol amine(2.344 g, 20 mmol) at the room temperature. After generation of hydrogen ceased, 2,3-dichloro-5-trifluoromethyl-pyridine (4.32 g, 20 mmol) was added at the room temperature. After exothermic reaction ceased, the mixture was further stirred for 2 hours at room temperature. Then the content was poured into water and extracted with ethyl acetate. Ethyl acetate layer was washed with water and dried over anhydrous sodium sulfate. The evaporation of the solvent gave 5.76 g of oil. Yield: 96.8%.

$^1$H NMR (CDCl$_3$, TMSP): 1.07(6H, t), 2.65(4H, q), 2.92(2H, t), 4.52(2H, t), 7.83(1H, s), 8.31(1H, s).

Step-2. Synthesis of N-(Phosphonomethyl)glycine. 2-(3-chloro-5-trifluoromethyl-2-pyridyloxy)-ethyl diethyl amine salt: Compound 6-24

A mixture of N-(phosphonomethyl)glycine (purity:95.5%, 442.4 mg, 2.5 mmol) in water (5 ml) was stirred and 2-(3-chloro-5-trifluoromethyl-2-pyridyloxy)-ethyl diethyl amine (743.8 mg, 2.5 mmol) was added at the room temperature. After warming for 1 hour to afford the clear solution, the content was cooled to room temperature and diluted with extra amount of water to give 5 ml of stock solution, which was directly used for the activity test.

Example 2

Synthesis of N-(Phosphonomethyl)glycine. O-2-aminopropyl-, O'-2-(methoxy)ethyl-, poly(propylene glycol) salt: Compound 6-33

A mixture of N-(phosphonomethyl)glycine (169 mg, 1 mmol) in water (5 ml) was stirred and warmed. Then O-2-aminopropyl-, O'-2-(methoxy)ethyl-, poly(propylene glycol) (600 mg, 1 mmol) in 1 ml of methanol was added and kept reflux for 1 hour. The mixture was evaporated to dryness to afford an oily product. Removing insoluble solid by dacantation gave about 500 mg of sticky oil.

Example 3

Synthesis of N-(Phosphonomethyl)glycine. O, O'-bis-(2-aminoethyl)-di-(ethylene glycol) salt: Compound 6-32

A mixture of N-(phosphonomethyl)glycine (169 mg, 1 mmol) in water (1 ml) was stirred and O, O'-bis-(2-aminoethyl)-di-(ethylene glycol) (220 mg, 1 mmol) was added to afford a clear solution. After stirring at room temperature for 1 hour, the mixture was evaporated and dried under the reduced pressure to afford 380 mg of solid, which showed the melting point 160–164° C.

Example 4

Synthesis of N-(Phosphonomethyl)glycine. Methoxy-poly-(oxyethylene/oxypropylene)-2-propryamine(molecular weight: 1000) salt: Compound 6-31

A mixture of N-(phosphonomethyl)glycine (purity:95.5%, 26.2 g, 148 mmol) in water (100 ml) was stirred and methoxy-poly-(oxyethylene/oxypropylene)-2-propylamine (molecular weight: 1000) was added to after the gentle exothermic reaction afford a clear solution. After stirring for further 10 minutes the extra water was added to make 300 ml volume of stock solution, which was directly used for the activity test.

Example 5

Synthesis of N-(Phosphonomethyl)glycine. Methoxy-poly-(oxyethylene/oxypropylene)-2-propylamine(molecular weight: 2000) salt: Compound 6-34

A mixture of N-(phosphonomethyl)glycine (purity:95.5%, 26.2 g, 148 mmol) in water (100 ml) was stirred and methoxy-poly-(oxyethylene/oxypropylene)-2-propylamine (molecular weight: 2000) was added to after the gentle exothermic reaction afford a clear solution. After stirring for further 10 minutes the extra water was added to make 500 ml volume of stock solution, which was directly used for the activity test.

HERBICIDAL ACTIVITY

The compounds of the present invention exhibit excellent herbicidal effects when used as an active ingredient of a herbicide. The herbicide can be used for a wide range of applications, for example on crop lands such as paddy fields, upland farms, orchards and mulberry fields, and non-crop lands such as forests, farm roads, playgrounds, and factory sites. The application method may be one suitably selected for foliar application.

The compounds of the present invention are capable of controlling noxious weeds including grass (gramineae) such as barnyardgrass (*Echinochloa crus-galli*), large crabgrass (*Digitaria sanguinalis*), green foxtail (*Setaria viridis*), giant foxtail (*Setaria faberi*), goosegrass (*Eleusine indica* L.), wild oat (*Avena fatua* L.), Johnsongrass (*Sorghum halepense*), quackgrass (*Agropyron repens*), alexandergrass (*Brachiaria plantaginea*), paragrass (*Panicum purpurascen*), sprangletop (*Leptochloa chinensis*) and red sprangletop (*Leptochloa panicea*); sedges (or Cyperaceae) such as rice flatsedge (*Cyperus iria* L.), purple nutsedge (*Cyperus rotundus* L.), Japanese bulrush (*Scirpus Juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon wapato (*Sagittaria pygmaea*), arrow-head (*Sagittaria trifolia*) and narrowleaf waterplantain (*Alisma canaliculatum*); pontederiaceae such as monochoria (*Monochoria vaginalis*) and monochoria species (*Monochoria korsakowii*); scrophulariaceae such as false pimpernel (*Lindernia pyxidaria*) and abunome (*Dopatrium Junceum*); lythraceae such as toothcup (*Rotala indica*) and red stem (*Ammannia multiflora*); and broadleaves such as redroot pigweed (*Amaranthus retroflexus*), velvetleaf (*Abutilon theophrasti*), morningglory (*Ipomoea hederacea*), lambsquarters (*Chenopodium album*), prickly sida (*Sida spinosa* L.), common purslane (*Portulaca oleracea* L.), common ragweed (*Ambrosia artemisiifolia* L.), slender amaranth (*Amaranthus viridis* L.), sicklepod (*Cassia obtusifolia*), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis* L.). Accordingly, it is useful for controlling noxious weeds non-selectively or selectively in the cultivation of a crop plant such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), Japanese lawngrass (*Zoysia Japonica* stend), peanut (*Arachis hypogaea* L.) or flax (*Linum usitatissimum* L.).

For use as herbicides, the active ingredients of this invention are formulated into herbicidal compositions by mixing herbicidally active amounts with inert ingredients known to the art to facilitate either the suspension, dissolution or emulsification of the active ingredient for the desired use. The type of formulation prepared recognizes the facts that formulation, crop and use pattern all can influence the activity and utility of the active ingredient in a particular use. Thus for agricultural use the present herbicidal compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These herbicidal formulations may be applied to the target area (where suppression of unwanted vegetation is the objective) as water or solvent diluted sprays. These formulation may contain as little as 0.1% to as much as 97% active ingredient by weight.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is conmercially available). After granulation the moisture content of granules is adjusted to an optimal level (generally less than 5%) and the product is sized to the desired mesh size.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Solution concentrates are solutions of the active ingredient (1 to 70%) in solvents which have sufficient solvency to dissolve the desired amount of active ingredient. Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient is made as a suspension concentrate (1–50% active ingredient) and the second active is made as a emulsifiable concentrate (0.1–20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The herbicidal compounds of this invention may be formulated or applied with insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UV protectants may be added in amounts of 0.01% to 20% to enhance the biological activity, stability, wetting, spreading on foliage or uptake of the active ingredients on the target area or to improve the suspensibility, dispersion, redispersion, emulsifiability, UV stability or other physical or physicochemical property of the active ingredient in the spray tank, spray system or target area.

The compositions of the present invention may be used in admixture with or in combination with other agricultural chemicals, fertilizers, adjuvants, surfactants, emulsifiers, oils, polymers or phytotoxicity-reducing agents such as herbicide safeners. In such a case, they may exhibit even better effects or activities. As other agricultural chemicals, herbicides, fungicides, antibiotics, plant hormones, plant growth regulators, insecticides, or acaricides may, for example, be mentioned. Especially with herbicidal compositions having the compounds of the present invention used in admixture with or in combination with one or more active ingredients of other herbicides, it is possible to improve the herbicidal activities, the range of application time(s) and the range of applicable weed types. Further, the compounds of the present invention and an active ingredient of another herbicide may be separately formulated so they may be mixed for use at the time of application, or both may be formulated together. The present invention covers such herbicidal compositions.

The blend ratio of the compounds of the present invention with the active ingredient of other herbicides can not generally be defined, since it varies depending on the time and method of application, weather conditions, soil type and type of formulation. However one active ingredient of other herbicide may be incorporated usually in an amount of 0.01 to 100 parts by weight, per one part by weight of the compounds of the present invention. Further, the total dose of all of the active ingredients is usually from 1 to 10000 g/ha, preferably from 5 to 3000 g/ha. The present invention covers such herbicidal compositions.

As the active ingredients of other herbicides, the following (common name) may be mentioned. Herbicidal compositions having the compounds of the present invention used in combination with other herbicides, may occasionally exhibit a synergistic effect.

1. Those that are believed to exhibit herbicidal effects by disturbing auxin activities of plants, including a phenoxy acetic acid type such as 2,4-D, 2,4-DB, 2,4-DP, MCPA, MCPP, MCPB or naproanilide (including the free acids, esters or salts thereof), an aromatic carboxylic type such as 2,3,6 TBA, dicamba, dichlobenil, a pyridine type such as picloram (including free acids and salts thereof), triclopyr or clopyralid and others such as naptalam, benazolin, quinclorac, quinmerac or diflufenzopyr (BAS 654H).
2. Those that are believed to exhibit herbicidal effects by inhibiting photosynthesis of plants including a urea type such as diuron, linuron, isoproturon, chlorotoluron, metobenzuron, tebuthiuron or fluometuron, a triazine type such as simazine, atrazine, cyanazine, terbuthylazine, atraton, hexazinone, metribuzin, simetryn, ametryn, prometryn, dimethametryn or triaziflam, a uracil type such as bromacil, terbacil or lenacil, an anilide type such as propanil or cypromid, a carbamate type such as desmedipham or phenmedipham, a hydroxybenzonitrile type such as bromoxynil or ioxynil, and others such as pyridate, bentazon and methazole.
3. A quaternary ammonium salt type such as paraquat, diquat or difenzoquat, which is believed to be converted to free radicals by itself to form active oxygen in the plant and thus to exhibit quick herbicidal effects.
4. Those which are believed to exhibit herbicidal effects by inhibiting chlorophyll biosynthesis in plants and abnormally accumulating a photosensitizing peroxide substance in the plant body, including a diphenyl ether type such as nitrofen, lactofen, acifluorfen-sodium, oxyfluorfen, fomesafen, bifenox, or chlomethoxyfen, a cyclic imide type such as chlorphthalim, flumioxazin, cinidon-ethyl, or flumiclorac-pentyl, and others such as oxadiazon, sulfentrazone, thidiazimin, azafenidin, carfentrazone, isopropazole (also referred to as JV-485), fluthiacet-methyl, pentoxazone, pyraflufen-ethyl, oxadiargyl and 2-chloro-5-[3,6-dihydro-2,6-dioxo-3-methyl-4-trifluoromethyl-1(2H)-pyrimidinyl]-benzoic acid-1-(allyloxycarbonyl)-1-methylethyl.
5. Those which are believed to exhibit herbicidal effects characterized by whitening activities by inhibiting chromogenesis of plants such as carotenoids including a pyridazinone type such as norflurazon, chloridazon or metflurazon, a pyrazol type such as pyrazolate, pyrazoxyfen or benzofenap, and others such as fluridone, fluramone, diflufencam, methoxyphenone, clomazone, amitrole, sulcotrione, mesotrione, isoxaflutole and isoxachlortole.
6. Those which exhibit herbicidal effects specifically to gramineous plants including an aryloxyphenoxypropionic acid type (either as a mixture of isomers or as a resolved isomer) such as diclofop-methyl, pyrofenop-sodium, fluazifop butyl or fluazifop-p-butyl, haloxyfop-methyl, quizalofop p-ethyl, quizalafop p-tefuryl, fenoxaprop ethyl or fenoxaprop-p-ethyl, flamprop-M-methyl or flamprop-m-isopropyl or cyhalofop-butyl and a cyclohexanedione type such as alloxydim-sodium, sethoxydim, clethodim, tepraloxydim or tralkoxydim.
7. Those which are believed to exhibit herbicidal effects by inhibiting amino acid biosynthesis of plants, including a sulfonylurea type such as chlorimuron-ethyl, nicosulfuron, metsulfuron-methyl, triasulfron, primisulfuron, tribenuron-methyl, chlorosulfuron, bensulfuron-methyl, sulfometuron-methyl, prosulfuron, halosulfuron or halosulfuron-methyl, thifensulfuron-methyl, rimsulfuron, azimsulfuron, flazasulfuron, imazosulfuron, cyclosulfamuron, flupyrsulfuron, iodosulfuron, ethoxysulfuron, flucarbazone, sulfosulfron, oxasulfuron a triazolopyrimidinesulfonamide type such as flumetsulam, metosulam, chloransulam or chloransulam-methyl, an imidazolinone type such as imazapyr, imazethapyr, imazaquin, imazamox, imazameth, imazamethabenz methyl, a pyrimidinesalicylic acid type such as pyrthiobac-sodium, bispyribac-sodium, pyriminobac-methyl or pyribenzoxim (LGC-40863), and others such as glyphosate, glyphosate-ammonium, glyphosate-isopropylamine, glyphosate-ethylenediamine or sulfosate.

8. Those which are believed to exhibit herbicidal effects by interfering with the normal metabolism of inorganic nitrogen assimilation such as glufosinate, glufosinate-ammonium, phosphinothricin or bialophos.

9. Those which are believed to exhibit herbicidal effects by inhibiting cell division of plant cells, including a dinitroaniline type such as trifluralin, oryzalin, nitralin, pendamethalin, ethafluralin, benefin and prodiamine, an amide type such as bensulide, napronamide, and pronamide, a carbamate type such as propham, chlorpropham, barban, and asulam, an organophosphorous type such as amiprofos-methyl or butamifos and others such as DCPA and dithiopyr.

10. Those which are believed to exhibit herbicidal effects by inhibiting protein synthesis of plant cells, including a chloroacetanilide type such as alachlor, metolachor (including combinations with safeners such as benoxacor, or resolved isomeric mixtures of metolachlor including safeners such as benoxacor) propachlor, acetochlor (including combinations with herbicide safeners such as dichlormid or MON 4660 or resolved isomeric mixtures of acetochlor containing safeners such as dichlormid or MON 4660), propisochlor or dimethenamid or an oxyacetamide type such as flufenacet.

11. Those in which the mode of action causing the herbicidal effects are not well understood including the dithiocarbamates such as thiobencarb, EPTC, diallate, triallate, molinate, pebulate, cycloate, butylate, vernolate or pro-sulfocarb and miscellaneous herbicides such as MSMA, DSMA, endothall, ethofumesate, sodium chlorate, pelargonic acid fosamine, and amicarbazone.

Test Example

A standard greenhouse herbicide activity screening system was used to evaluate the herbicidal efficacy and crop safety of these test compounds. Four broadleaf weed species, lambsquarters (*Chenopodium album,* CHEAL), velvetleaf (*Abutilon theophrasti,* ABUTH), common ragweed (*Ambrosia artemisiifolia,* AMBEL), and ivyleaf morningglory (*Ipomoea hederacea,* IPOHE), and four grass weed species including green foxtail (*Setaria viridis,* SETVI), barnyardgrass (*Echinochloa crus-galli,* ECHCG), johnsongrass (*Sorghum halepense,* SORHA), and large crabgrass (*Digitaria sanguinalis,* DIGSA) were used as test species.

Because the salts of glyphosate are known to be inactive when applied as a soil treatment, only POST emergent sprays were applied.

For the post-emerge tests, seeds were planted 10–28 days prior to the test to allow emergence and good foliage development prior to application of the test substances. At the time of the post-emerge application, plants of all species were usually at the 2–4 leaf stage of development.

All test compounds were dissolved in water and applied to the test units in a volume of 187 l/ha. A commercial non-ionic surfactant was also included (0.25% v/v) to enhance wetting of the leaf surfaces of target plants. Test materials were applied at rates ranging from 105 g acid equivalent/ha to 1680 g acid equivalent/ha using a track sprayer equipped with a TJ8001E even flow flat fan spray nozzle. Plants were arranged on a shelf so that the top of the canopy was 40–45 cm below the nozzle. Pressurized air was used to force the test solution through the nozzle as it was mechanically advanced over the top of all test plants. This application simulates a typical commercial field herbicide application.

Post-emerge test units were always bottom-watered. At 14 days after application of the test materials, phytotoxicity ratings were recorded. A rating scale of 0–100 was used as previously described in *Research Methods in Weed Science,* 2nd edition, B. Truelove, Ed., Southern Weed Science Society, Auburn University, Auburn, Alabama, 1977. Briefly, "0" corresponds to no damage and "100" corresponds to complete death of all plants in the test unit.

Tables 7–10 show the activity (% Control 0–100) of representative compounds of this invention on grassy weed species, compared to the prior art compound glyphosate-isopropylamine and glyphosate-ethanolamine salts.

TABLE 7

Efficacy of compounds on *Setaria viridis* (green foxtail).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 105 | 30 | 15 | 50 | 30 | 10 | 40 | 10 | 10 | 5 | 0 |
| 210 | 50 | 40 | 70 | 85 | 85 | 90 | 40 | 70 | 30 | 35 |
| 420 | 99 | 98 | 95 | 99 | 99 | 95 | 90 | 85 | 50 | 70 |
| 840 | 100 | 99 | 99 | 95 | 99 | 85 | 100 | 90 | 70 | 98 |

TABLE 8

Efficacy of compounds on *Echinochloa crus-galli* (barnyardgrass).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 105 | 40 | 15 | 0 | 15 | 20 | 10 | 20 | 20 | 0 | 0 |
| 210 | 75 | 60 | 60 | 75 | 75 | 65 | 50 | 65 | 10 | 10 |

TABLE 8-continued

Efficacy of compounds on *Echinochloa crus-galli* (barnyardgrass).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 420 | 96 | 90 | 80 | 95 | 99 | 75 | 75 | 75 | 40 | 50 |
| 840 | 99 | 99 | 99 | 100 | 99 | 90 | 99 | 85 | 80 | 95 |

TABLE 9

Efficacy of compounds on *Sorghum halepense* (johnsongrass, seedling).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 105 | 80 | 30 | 20 | 50 | 30 | 10 | 40 | 40 | 0 | 0 |
| 210 | 95 | 50 | 75 | 90 | 90 | 70 | 85 | 65 | 10 | 10 |
| 420 | 99 | 99 | 85 | 100 | 99 | 85 | 99 | 90 | 30 | 25 |
| 840 | 100 | 100 | 100 | 100 | 100 | 99 | 99 | 95 | 70 | 99 |

TABLE 10

Efficacy of compounds on *Digitaria sanguinalis* (large crabgrass).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 105 | 40 | 30 | 30 | 40 | 30 | 30 | 20 | 30 | 0 | 0 |
| 210 | 65 | 40 | 45 | 50 | 60 | 50 | 30 | 45 | 10 | 50 |
| 420 | 65 | 65 | 55 | 70 | 80 | 65 | 60 | 60 | 35 | 75 |
| 840 | 80 | 85 | 99 | 90 | 75 | 85 | 85 | 60 | 75 | 85 |

Compounds of this invention show activity against grassy weeds equal too or greater than glyphosate-isopropylamine or glyphosate-ethanolamine. Tables 11–14 show the activity (% Control, 0–100) of representative compounds of this invention on broadleaf weed species, compared to the prior art compound glyphosate-isopropylamine and glyphosate-ethanolamine salts.

TABLE 11

Efficacy of compounds on *Abutilon theophrasti* (velvetleaf).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 105 | 10 | 15 | 15 | 15 | 10 | 10 | 15 | 20 | 5 | 0 |
| 210 | 40 | 45 | 40 | 65 | 40 | 40 | 45 | 40 | 15 | 5 |
| 420 | 70 | 70 | 50 | 70 | 80 | 65 | 60 | 60 | 40 | 50 |
| 840 | 80 | 90 | 80 | 85 | 90 | 70 | 85 | 60 | 60 | 70 |

TABLE 12

Efficacy of compounds on *Ipomoea hederacea* (ivyleaf morningglory).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 105 | 30 | 15 | 10 | 10 | 10 | 10 | 15 | 20 | 5 | 0 |
| 210 | 30 | 30 | 30 | 40 | 40 | 40 | 35 | 60 | 15 | 30 |
| 420 | 60 | 50 | 50 | 50 | 60 | 60 | 50 | 60 | 25 | 50 |
| 840 | 75 | 80 | 75 | 80 | 75 | 70 | 80 | 85 | 60 | 70 |

TABLE 13

Efficacy of compounds on *Chenopodium alhum* (common lambsquarters).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 105 | 15 | 10 | 20 | 5 | 10 | 10 | 60 | 10 | 0 | 0 |
| 210 | 40 | 20 | 30 | 60 | 35 | 45 | 50 | 50 | 0 | 0 |
| 420 | 65 | 50 | 70 | 75 | 75 | 55 | 65 | 60 | 15 | 10 |
| 840 | 75 | 75 | 75 | 80 | 75 | 65 | 70 | 90 | 55 | 70 |

TABLE 14

Efficacy of compounds on *Ambrosia artemisiifolia* (common ragweed).

| Acid Equivalents Applied grams/ha | 6-13 | 6-30 | 6-31 | 6-34 | 6-33 | 6-32 | 6-35 | 6-37 | Isopropyl Amine Salt | Ethanol Amine Salt |
|---|---|---|---|---|---|---|---|---|---|---|
| 105 | 5 | 5 | 5 | 5 | 5 | 10 | 20 | 5 | 0 | 0 |
| 210 | 30 | 15 | 30 | 40 | 35 | 30 | 30 | 40 | 20 | 0 |
| 420 | 55 | 40 | 50 | 60 | 60 | 50 | 50 | 50 | 15 | 35 |
| 840 | 65 | 75 | 70 | 80 | 70 | 65 | 70 | 70 | 60 | 80 |

Compounds of this invention show activity against broadleaf weeds equal too or greater than glyphosate-isopropylamine salt or glyphosate-ethanolamine salt. Tables 15–18 show the activity of representative two- and three-way combinations of actives in diamines or triamines, on grassy weed species, compared to the prior art compound glyphosate-isopropylamine salt (alone, or in the commercial formulation Roundup Ultra™)

TABLE 15

Efficacy of two- and three-way combinations on *Setaria vindis* (green foxtail).

| Acid Equivalents Applied Grams/ha | 6-53 | 6-54 | 6-56 | 6-59 | 6-60 | 6-61 | Isopropyl Amine Salt | Roundup Ultra ™ |
|---|---|---|---|---|---|---|---|---|
| 105 | 80 | 65 | 65 | 85 | 75 | 70 | 50 | 65 |
| 210 | 95 | 95 | 85 | 85 | 90 | 90 | 70 | 75 |
| 420 | 99 | 98 | 100 | 85 | 99 | 90 | 80 | 99 |
| 840 | 100 | 100 | 100 | 85 | 100 | 100 | 99 | 100 |

TABLE 16

Efficacy of two- and three-way combinations on *Echinochloa crus-galli* (barnyardgrass).

| Acid Equivalents Applied Grams/ha | 6-53 | 6-54 | 6-56 | 6-59 | 6-60 | 6-61 | Isopropyl Amine Salt | Roundup Ultra ™ |
|---|---|---|---|---|---|---|---|---|
| 105 | 65 | 70 | 90 | 60 | 75 | 55 | 0 | 65 |
| 210 | 95 | 95 | 99 | 95 | 99 | 75 | 55 | 80 |
| 420 | 98 | 95 | 100 | 95 | 99 | 100 | 65 | 99 |
| 840 | 100 | 100 | 100 | 100 | 100 | 100 | 100 | 100 |

TABLE 17

Efficacy of two- and three-way combinations on *Sorghum halepense* (johnsongrass, seedling).

| Acid Equivalents Applied Grams/ha | 6-53 | 6-54 | 6-56 | 6-59 | 6-60 | 6-61 | Isopropyl Amine Salt | Roundup Ultra ™ |
|---|---|---|---|---|---|---|---|---|
| 105 | 80 | 60 | 50 | 0 | 85 | 55 | 0 | 80 |
| 210 | 99 | 85 | 90 | 99 | 99 | 90 | 50 | 100 |
| 420 | 100 | 98 | 99 | 100 | 100 | 99 | 75 | 100 |
| 840 | 100 | 100 | 99 | 100 | 100 | 100 | 100 | 100 |

TABLE 18

Efficacy of two- and three-way combinations on *Digitaria sanguinalis* (large crabgrass).

| Acid Equivalents Applied Grams/ha | 6-53 | 6-54 | 6-56 | 6-59 | 6-60 | 6-61 | Isopropyl Amine Salt | Roundup Ultra ™ |
|---|---|---|---|---|---|---|---|---|
| 105 | 80 | 80 | 70 | 65 | 70 | 55 | 40 | 65 |
| 210 | 85 | 90 | 75 | 70 | 75 | 70 | 60 | 75 |
| 420 | 95 | 90 | 95 | 90 | 90 | 85 | 75 | 90 |
| 840 | 98 | 90 | 99 | 99 | 100 | 100 | 90 | 100 |

Two- and three-way combinations of this invention show activity against grassy weeds superior to the isopropylamine salt of glyphosate and equal to the commercial Roundup Ultra™ formulation. Tables 19–22 show the activity of representative two- and three-way combinations of actives in diamines or triamines, on broadleaf weed species, compared to the prior art compound glyphosate-isopropylamine salt (alone, or in the commercial formulation Roundup Ultra™).

TABLE 19

Efficacy of two- and three-way combinations on *Abuilon theophrasti* (velvetleaf).

| Acid Equivalents Applied Grams/ha | 6-53 | 6-54 | 6-56 | 6-59 | 6-60 | 6-61 | Isopropyl Amine Salt | Roundup Ultra ™ |
|---|---|---|---|---|---|---|---|---|
| 105 | 50 | 65 | 60 | 75 | 50 | 50 | 30 | 65 |
| 210 | 50 | 75 | 70 | 90 | 65 | 70 | 60 | 75 |
| 420 | 85 | 80 | 80 | 95 | 75 | 70 | 65 | 80 |
| 840 | 85 | 95 | 90 | 99 | 70 | 90 | 70 | 95 |

TABLE 20

Efficacy of two- and three-way combinations on *Ipomoea hederacea* (ivyleaf morningglory).

| Acid Equivalents Applied Grams/ha | 6-53 | 6-54 | 6-56 | 6-59 | 6-60 | 6-61 | Isopropyl Amine Salt | Roundup Ultra ™ |
|---|---|---|---|---|---|---|---|---|
| 105 | 90 | 75 | 99 | 95 | 98 | 100 | 25 | 65 |
| 210 | 95 | 90 | 99 | 95 | 98 | 100 | 40 | 65 |
| 420 | #OO | 95 | 99 | 95 | 99 | 100 | 80 | 85 |
| 840 | 100 | 99 | 100 | 100 | 99 | 100 | 85 | 90 |

TABLE 21

Efficacy of two- and three-way combinations on *Chenopodium album* (common lambsquarters).

| Acid Equivalents Applied Grams/ha | 6-53 | 6-54 | 6-56 | 6-59 | 6-60 | 6-61 | Isopropyl Amine Salt | Roundup Ultra ™ |
|---|---|---|---|---|---|---|---|---|
| 105 | 90 | 80 | 99 | 100 | 99 | 98 | 50 | 70 |
| 210 | 95 | 95 | 99 | 10() | 100 | 98 | 50 | 70 |
| 420 | 99 | 98 | 99 | 100 | 100 | 100 | 60 | 90 |
| 840 | 100 | 99 | 100 | 100 | 100 | 98 | 75 | 90 |

TABLE 22

Efficacy of two- and three-way combinations on *Ambrosia artemisiifolia* (common ragweed).

| Acid Equivalents Applied Grams/ha | 6-53 | 6-54 | 6-56 | 6-59 | 6-60 | 6-61 | Isopropyl Amine Salt | Roundup Ultra ™ |
|---|---|---|---|---|---|---|---|---|
| 105 | 0 | 85 | 80 | 90 | 75 | 65 | 50 | 65 |
| 210 | 90 | 99 | 90 | 99 | 80 | 70 | 60 | 70 |
| 420 | 90 | 99 | 99 | 100 | 85 | 75 | 65 | 70 |
| 840 | 100 | 100 | 100 | 100 | 100 | 95 | 75 | 90 |

Two- and three-way combinations of this invention show activity against broadleaf weeds superior to the isopropyl amine salt of glyphosate and the commercial Roundup Ultra™ formulation.

What is claimed is:

1. A compound of the following formula I

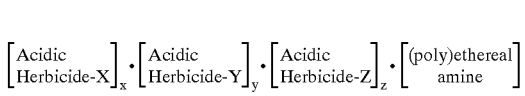

wherein x, y, and z are integers from 0 to 3 with the proviso that $0 < x+y+z \leq 3$;

acidic Herbicide-X, Acidic Herbicide-Y, and Acidic Herbicide-Z, same or different that can be used in compositions of the present invention and possess the dissociable proton(s) in their structures are selected from the group consisting of:

acifluorfen, asulam, benazolin, bentazon, bilanafos, bromacil, bromoxynil, chloramben, clopyralid, cyhalofop, 2,4-D, 2,4-DB, dalapon, dicamba, dichlorprop, diclofop, DNOC, endothall, fenac, fenoxaprop, flamnprop, fluazifop, flumiclorac, fluoroglycofen, fomesafen, fosamine, glufosinate, glyphosate, haloxyfop, imazameth, imazamethabenz, imazamox, imazapic, imazapyr, imazaquin, imazethapyr, ioxynil, MCPA, MCPB, MCPP, mecoprop, methylarsonic acid, naptalam, nonanoic acid, picloram, quinclorac, quizalofop, sulfamic acid, 2,3,6-TBA, TCA, and triclopyr;

the (poly)ethereal amine is at least one selected from compounds of formula $II^1$ through $II^5$:

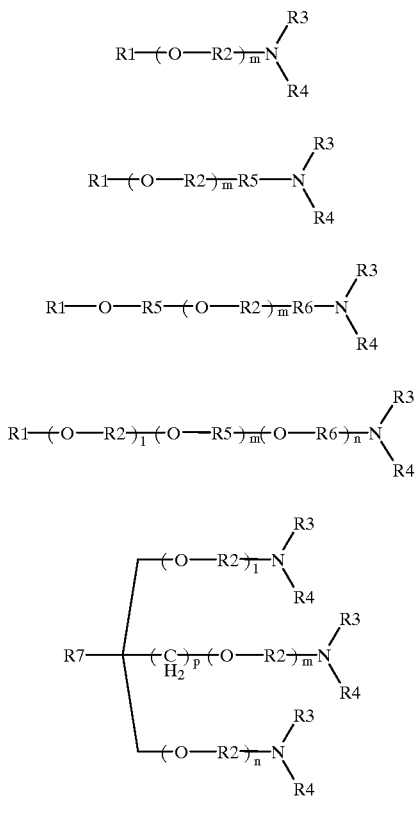

wherein $R_1$ is a hydrogen, a $C_{1-26}$ alkyl, a $C_{2-6}$ alkenyl, a $C_{2-6}$ alkynyl branched-chain or straight-chain which may or may not be substituted with one or more halogen, hydroxy, $C_{1-6}$ alkoxy, $(C_{1-6}$ alkyl-$)_q$-amino (q is an integer of 0, 1, or 2), morpholino, or $C_{1-6}$ alkoxycarbonyl group, an aryl, or a heteroaryl which may or may not be substituted with $C_{1-6}$ alkyl, $C_{1-6}$ haloalkyl, halogen, $C_{1-6}$ alkoxy, $(C_{1-6}$ alkyl-$)_q$-amino ($q$ is an integer of 0, 1, or 2), nitro, or $C_{1-6}$ alkoxycarbonyl group;

$R_2$, $R_5$, and $R_6$ are independently $C_{1-8}$ alkylene branched-chain or straight-chain, which may contain imine or ether linkage therein and may be substituted by a $C_{1-6}$ alkyl group;

$R_3$ and $R_4$ are a hydrogen atom or a $C_{1-6}$ alkyl group, which may be branched or straight and may or may not be substituted with one or more $C_{1-6}$ alkoxy, or a group of $R_1$—(—O—$R_2$—$)_{m'}$—O—;

$R_7$ is a hydrogen or a $C_{1-6}$ alkyl group;

l, m and n is a number from 1 to about 500;

m' is a number from 0 to about 35;

p is an integer of 0 or 1;

when m is 1, none of $R_1$, $R_3$, and $R_4$ is H and further $R_2$ is not ethylene.

2. The compound according to claim 1 wherein $R_1$ is a $C_{1-26}$ alkyl, $R_2$, $R_5$, and $R_6$ are independently a $C_{1-8}$alkylene branched-chain or straight-chain, $R_3$ and $R_4$ are a hydrogen, each of l, m and n is a integer from 5 through 300.

3. The compound according to claim 1 wherein $R_1$ is a methyl, $R_2$, $R_5$, and $R_6$ are independently a $C_{1-38}$alkylene branched-chain or straight-chain, $R_3$ and $R_4$ are a hydrogen, each of l, m and n is a integer from 5 through 35.

4. A herbicidal composition which comprises a herbicidally effective amount of a compound of claim 1 and carrier.

5. A method for controlling undesired vegetation which comprises applying to a locus to be protected a herbicidally effective amount of a compound of claim 1.

6. A process for preparing a compound of the following formula

wherein x, y, and z are integers from 0 to 3 with the proviso that $0<x+y+z\leq3$;

acidic Herbicide-X, Acidic Herbicide-Y, and Acidic Herbicide-Z, same or different that can be used in compositions of the present invention and possess the dissociable proton(s) in their structures are selected from the group consisting of:

acifluorfen, asulam, benazolin, bentazon, bilanafos, bromacil, bromoxynil, chloramben, clopyralid, cyhalofop, 2,4-D, 2,4-DB, dalapon, dicamba, dichlorprop, diclofop, DNOC, endothall, fenac, fenoxaprop, flamprop, fluazifop, flumiclorac, fluoroglycofen, fomesafen, fosamine, glufosinate, glyphosate, haloxyfop, imazameth, imazamethabenz, imazamox, imazapic, imazapyr, imazaquin, imazethapyr, ioxynil, MCPA, MCPB, MCPP, mecoprop, methylarsonic acid, naptalam, nonanoic acid, picloram, quinclorac, quizalofop, sulfamic acid, 2,3,6-TBA, TCA, and triclopyr;

the (poly)ethereal amine is at least one selected from compounds of formula $II^1$ through $II^5$:

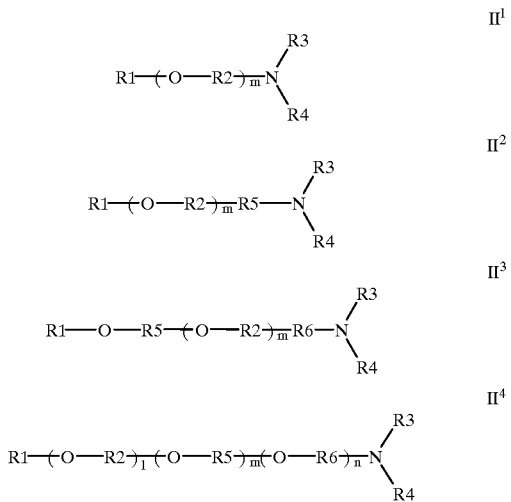

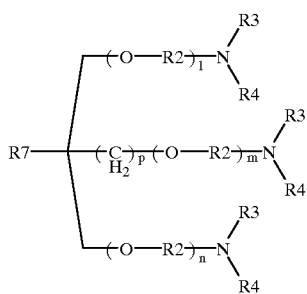

wherein $R_1$ is a hydrogen, a $C_{1-26}$ alkyl, a $C_{2-6}$ alkenyl, a $C_{2-6}$ alkynyl branched-chain or straight-chain which may or may not be substituted with one or more halogen, hydroxy, $C_{1-6}$ alkoxy, ($C_{1-6}$ alkyl-)q-amino (q is an integer of 0, 1, or 2), morpholino, or $C_{1-6}$ alkoxycarbonyl group, an aryl, or a heteroaryl which may or may not be substituted with $C_{1-6}$ alkyl, $C_{1-6}$ haloalkyl, halogen, $C_{1-6}$ alkoxy, ($C_{1-6}$ alkyl-)$_q$-amino ($q$ is an integer of 0, 1, or 2), nitro, or $C_{1-6}$ alkoxycarbonyl group;

$R_2$, $R_5$, and $R_6$ are independently $C_{1-8}$alkylene branched-chain or straight-chain, which may contain imine or ether linkage therein and may be substituted by a $C_{1-6}$ alkyl group;

$R_3$ and $R_4$ are a hydrogen atom or a $C_{1-6}$ alkyl group, which may be branched or straight and may or may not be substituted with one or more $C_{1-6}$ alkoxy, or a group of $R_1$—(—O—$R_2$—)$_{m'}$—O—;

$R_7$ is a hydrogen or a $C_{1-6}$ alkyl group;

l, m and n is a number from 1 to about 500;

m' is a number from 0 to about 35;

p is an integer of 0 or 1;

when m is 1, none of $R_1$, $R_3$, and $R_4$ is H and further $R_2$ is not ethylene, which comprises reacting acidic herbicide(s) with an amine of the above formula II$^1$ through II$^5$.

* * * * *